United States Patent
Mostafa et al.

(10) Patent No.: US 11,045,792 B1
(45) Date of Patent: Jun. 29, 2021

(54) HIGHLY EFFICIENT NANOSIZED MESOPOROUS CUMGAL TERNARY OXIDE CATALYST

(71) Applicant: King Abdulaziz University, Jeddah (SA)

(72) Inventors: Mohamed Mokhtar Mohamed Mostafa, Jeddah (SA); Budoor Fadl Ali Alhashedi, Jeddah (SA); Heba Abbas Kashmery, Jeddah (SA); Nesreen Said Ismail Ahmed, Jeddah (SA); Tamer Said Sayed Saleh, Jeddah (SA); Katabathini Narasimharao, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/038,367

(22) Filed: Sep. 30, 2020

(51) Int. Cl.
*B01J 23/78* (2006.01)
*C07C 201/12* (2006.01)
*C07C 205/06* (2006.01)

(52) U.S. Cl.
CPC ............. *B01J 23/78* (2013.01); *C07C 201/12* (2013.01); *C07C 205/06* (2013.01); *C07C 2523/78* (2013.01)

(58) Field of Classification Search
CPC . C07C 201/12; C07C 201/205; C07C 201/06; C07C 2523/78; B01J 23/78
See application file for complete search history.

(56) References Cited

PUBLICATIONS

Narasimharao et al, Microwave assisted efficient protocol for the classic Ullmann homocoupling reaction using Cu—Mg—Al hydrotalcite catalysts (Journal of Molecular Catalysis A: Chemical 379 (2013) 152-162).*

Barrault et al., On the catalytic properties of mixed oxides obtained from the Cu—Mg—Al LDH precursors in the process of hydrogenation of the cinnamaldehyde (Applied Catalysis A: General 262 (2004) 43-51).*

\* cited by examiner

*Primary Examiner* — Jafar F Parsa
(74) *Attorney, Agent, or Firm* — W & C IP

(57) ABSTRACT

Highly efficient nanosized mesoporous CuMgAl ternary oxide catalysts are provided.

9 Claims, 7 Drawing Sheets
(6 of 7 Drawing Sheet(s) Filed in Color)

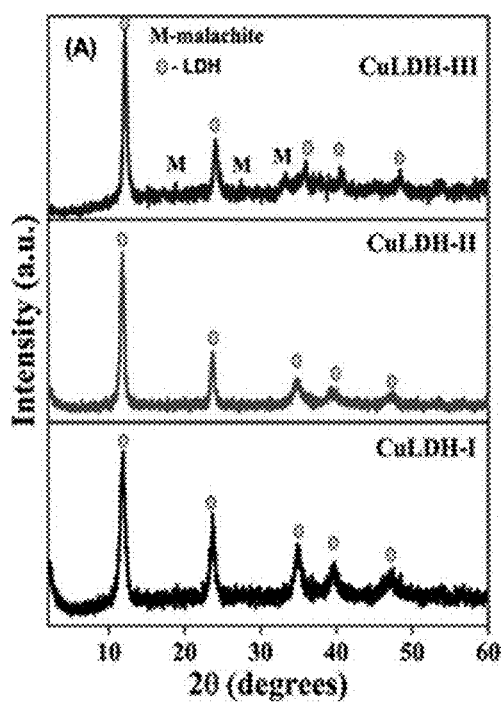
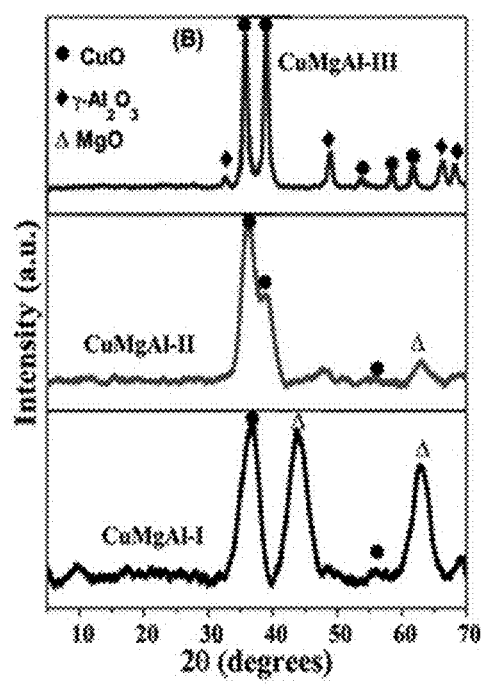
Figure 1A                    Figure 1B

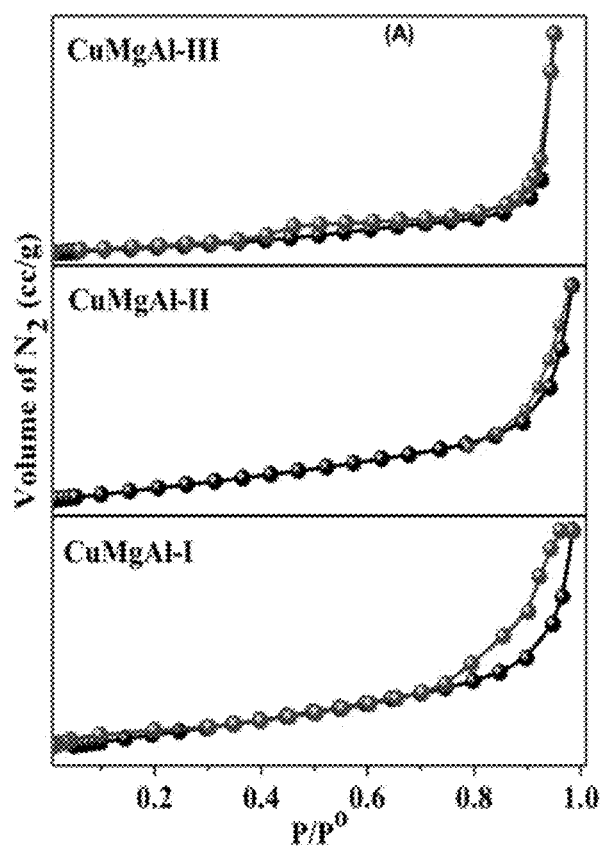
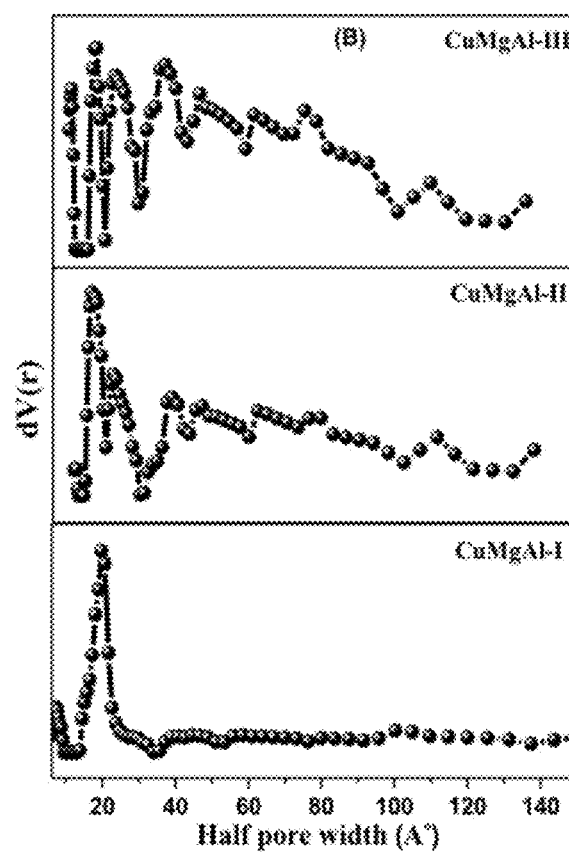
Figure 3A                    Figure 3B

HIGHLY EFFICIENT NANOSIZED MESOPOROUS CUMGAL TERNARY OXIDE CATALYST

BACKGROUND OF THE INVENTION

Field of the Invention

The invention generally relates to improved catalysts. In particular, the invention provides new nanosized mesoporous CuMgAl ternary oxide catalysts that are highly efficient.

Description of Related Art

The Henry reaction continues to attract attention in synthetic organic chemistry research.[1-3] With the development of suitable chiral catalysts, the reaction was established as a viable approach in asymmetric organic molecules synthesis, particularly in the field of pharmaceuticals and experimental therapeutics, in which the biological activities of compounds depend on their relative chirality.[2] Traditional approaches for C—C coupling in the Henry reaction involving soluble inorganic bases such as alkali-metal/alkaline-earth-metal hydroxides, carbonates, bicarbonates, alkoxides, ethoxides, and organic bases such as primary, secondary, and tertiary amines frequently produce dehydration products.[1] Moreover, control of the basicity of the reaction medium is vital to obtain higher yields of β-nitro alcohols. However, the reported methodologies in the literature suffer from the drawback of the production of moderate yields of alcohols over long reaction times.[2,3] Stoichiometric organic synthetic methods, which have largely been applied so far, give rise to large quantities of inorganic salts as byproducts, disposal of which has serious consequences in the environment.[4] The homogeneous catalytic procedures described in the literature have many drawbacks, such as the removal of waste and the difficulty in recovering the catalyst from the products. Potentially, many byproducts can be formed during the selective synthesis of 2-nitroalkanols, such as aldol olefins and their polymers and Cannizzaro products, depending on the nature of the base.[5]

The Henry reaction has undergone significant developments, for example, silyl nitronates have been used in the presence of fluoride ions or alternatively α,α-doubly deprotonated primary nitroalkanes.[6] These reactions are valued in the stereo-selective synthesis of vicinal amino alcohols, but are performed under severe conditions that reduce the diastereoselectivity of the reactions with aromatic aldehydes. Therefore, to achieve better yields and diastereoselectivity in the synthesis of 2-nitro alcohols, it is vital to investigate the use of heterogeneous catalysts with basic sites.[7] Although there have been outstanding advances in the development of heterogeneous catalysts for the Henry reaction,[8,9] the development of an environmentally friendly process and a robust environmentally benign catalyst to synthesize novel Henry reaction products remains a challenge.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

Provided herein are nanosized mesoporous CuMgAl ternary oxide catalysts. The catalysts were prepared by thermal decomposition of CuMgAl-layered double hydroxides at 500° C. with nominal Cu/Mg/Al ratios of 1:1:1 (Cu-LDH-I), 1.5:0.5:1 (Cu-LDH-II), and 2:0:1 (Cu-LDH-III). The synthesized catalysts were characterized by inductively coupled plasma atomic emission spectroscopy (ICP-AES), X-ray diffraction (XRD), X-ray photoelectron spectroscopy (XPS), scanning electron microscopy (SEM), high-resolution transmission electron microscopy (HRTEM), Fourier transform infrared (FTIR) spectroscopy, $CO_2$-TPD, and $N_2$ physisorption analysis techniques. The catalytic activity of the synthesized materials was investigated for the Henry reaction between nitromethane and numerous aldehyde derivatives under ultrasonic irradiation. The three CuMgAl ternary oxide catalysts exhibited a high catalytic activity, forming nitro alcohol products with 100% atom economy. The CuMgAl-I catalyst derived from Cu-LDH-I offered high turnover frequencies (TOFs in the synthesis of all the nitro alcohols in shorter reaction times). The superior catalytic activity of the CuMgAl-I sample is attributed to the synergistic effect between the physicochemical properties of the catalysts and ultrasonic irradiation. The HRTEM analysis of the used CuMgAl-I catalyst revealed the evidence for cavitation collapse, which causes localized deformation and surface erosion. Moreover, the synthesized catalysts also exhibited robust sustainable activity that resisted deactivation over repeated usage. This represents a novel strategy for the solvent-free green synthesis of nitro-alcohols by the Henry reaction with 100% atom economy.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A and B. XRD patterns of (A) as-synthesized CuLDH precursor samples and (B) calcined CuMgAl-I, CuMgAl-II, and CuMgAl-III catalysts.

FIGS. 3A and B. (A) $N_2$ adsorption-desorption isotherms and (B) pore size distribution patterns of ternary CuMgAl oxide samples.

DETAILED DESCRIPTION

Figure 2:
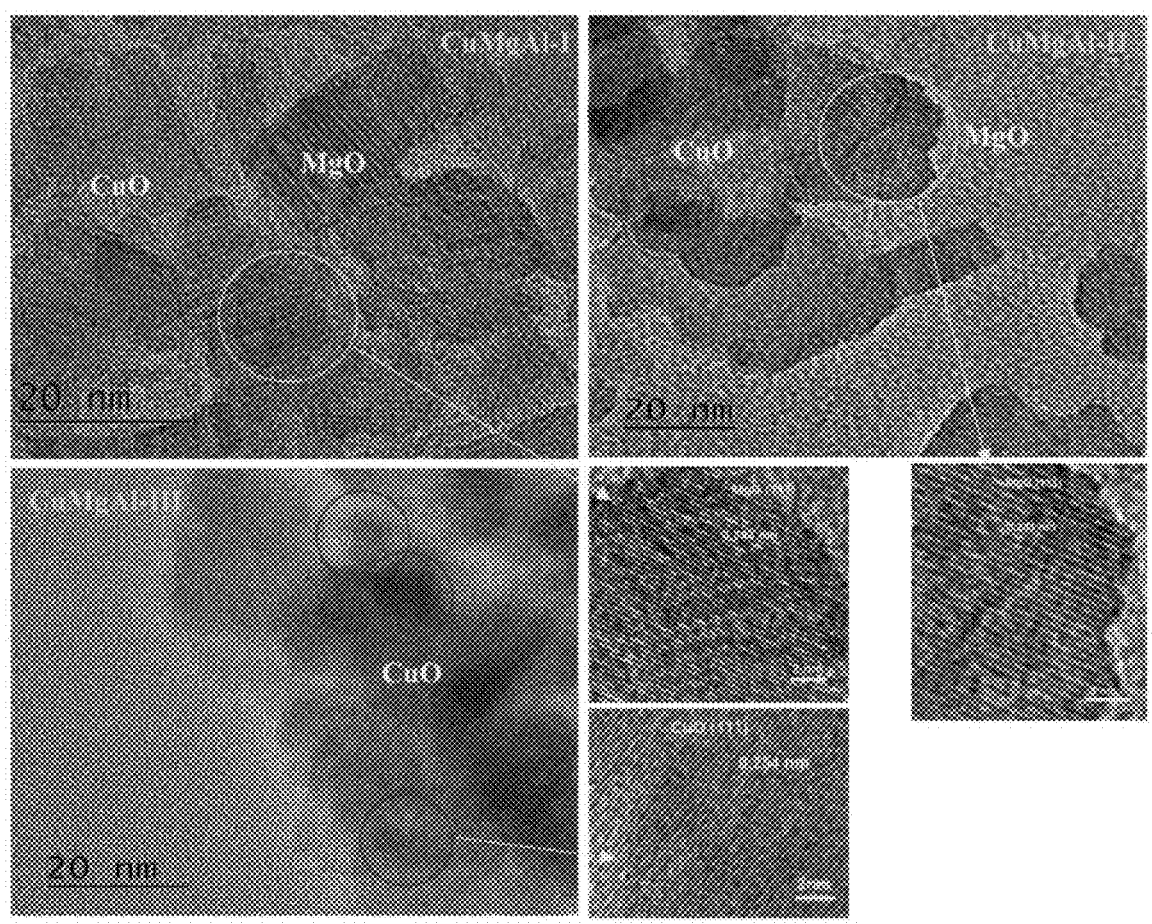
FIG. 2. HRTEM images of calcined CuMgAl samples.

The present disclosure provides three nanosized mesoporous CuO/MgAlOx catalysts, CuMgAl-I, CuMgAl-II, and CuMgAl-III. The catalysts were prepared from CuMgAl-layered double hydroxides and were employed for the exemplary Henry reaction between nitromethane and a variety of benzaldehydes assisted by ultrasound irradiation. The results showed the synthesis of alcohols with 100% atom economy and high turnover frequencies (TOFs). A thorough characterization of catalysts was performed to understand the relationship between the physicochemical properties of the catalysts and their catalytic functionality.

Definitions

A mesoporous material is a material containing pores with diameters between 2 and 50 nm, according to IUPAC nomenclature.

Calcination refers to heating a solid to high temperatures in air or oxygen, generally for the purpose of removing impurities or volatile substances and/or to bring about a thermal decomposition.

Ultrasonic energy or radiation refers to sound waves whose frequencies are higher than those of waves normally audible to the human ear. The angular frequencies of ultrasonic waves lie from about $10^5$ sec$^{-1}$ to about $3 \times 10^9$ sec$^{-1}$, the former value representing the limit of audibility of the human ear, i.e. a frequency greater than 20,000 Hz Ultrasound energy, usually simply known as "ultrasound", is a type of mechanical energy characterized by vibrating or moving particles within a medium.

Atom economy (atom efficiency/percentage) is the conversion efficiency of a chemical process in terms of all atoms involved and the desired products produced.

The Catalysts

New CuMgAl catalysts are provided and are denominated CuMgAl-I, CuMgAl-II, and CuMgAl-III herein. The three catalysts differ in chemical composition, namely in the amounts of Cu, Mg, and Al in each (e.g. the Cu/Mg/Al ratio), as follows:

for CuMgAl-I the ratio is 1:1:1;

for CuMgAl-II the ratio is 1.5:0.5:1; and for CuMgAl-III the ratio is 2:0:1. In other words, the CuMgAl-III sample does not contain any Mg; it contains only Cu and Al.

The morphologies of the catalysts also differ, with CuMgAl-I and CuMgAl-II being composed of small irregular sheets of Mg/Al/Cu oxides (which could be beneficial for a high exposure of active $Cu^{2+}$ sites). The sheets have a size ranging from about 5 to about 30 nm, such as from about 10 to about 25 nm, e.g. sizes of sheets in a batch of catalyst are about 10, 11, 12, 13, 14, 15, 16, 17, 18, 19, 20, 21, 22, 23, 24 or 25 nm, including all decimal fractions in between to e.g. 0.1 decimal places. In some aspects, sizes in a batch of catalyst range from about 10.5 to 24.5 nm. Without being bound by theory, it is believed that larger sheet particles are likely due to the presence of Mg—Al—O, whereas smaller particles are likely made up of CuO.

The surface areas of the catalysts also differ. For example:
CuMgAlI exhibited a relatively high surface area ranging from about 70 to 90 m$^2$ g$^{-1}$, such as about 70, 75, 80, 85 or 90 nm. In some aspects, the surface area is 78 m$^2$ g$^{-1}$;
CuMgAlII exhibited a surface area ranging from about 60 to 80 m$^2$ g$^{-1}$ such as about 60, 65, 70, 75 or 80 nm. In some aspects, the surface area is 70 m$^2$ g$^{-1}$;
CuMgAlIII exhibited a surface area ranging from about 10 to 30 m$^2$ g$^{-1}$ such as about 10, 15, 20, 25 or 30 nm. In some aspects, the surface area is 20 m$^2$ g$^{-1}$.

The pore volumes of the catalysts also differ. For example:
CuMgAlI exhibited a pore volume ranging from about 0.1 to 0.3 m$^2$ g$^{-1}$ such as about 0.1, 0.15, 0.2, 0.25 and 0.3, including all decimal fractions to 0.001 decimal places in between. In some aspects, the pore volume is about 0.210 cm$^3$ g$^{-1}$.

CuMgAlII exhibited a pore volume ranging from about 0.1 to 0.25 m$^2$ g$^{-1}$ such as about 0.1, 0.15, 0.2, and 0.25, including all decimal fractions to 0.001 decimal places in between. In some aspects, the pore volume is about 0.194 cm$^3$ g$^{-1}$;
CuMgAlIII exhibited a pore volume ranging from about 0.1 to 0.2 m$^2$ g$^{-1}$ such as about 0.1, 0.15 and 0.2, including all decimal fractions to 0.001 decimal places in between. In some aspects, the pore volume is about 0.153 cm$^3$ g$^{-1}$.

The differences in composition and physical properties of the three catalysts confer different catalytic abilities on each as described below and in the Examples section.

Methods of Making the Catalysts

The catalysts were prepared from CuMgAl-layered double hydroxides (LDHs).

The copper/magnesium/aluminum layered double hydroxides (Cu-LDHs) are typically prepared by the co-precipitation method. Two solutions, namely, solution A, containing the calculated amounts of metal (Cu, Mg, and Al) nitrates, and solution B, containing the precipitating agents (e.g. NaOH and Na$_2$CO$_3$) are added slowly and simultaneously, with stirring, to a flask containing distilled water at a temperature of from about 40 to about 60° C., such as about 50° C. A constant pH value ranging from about 9 to 11, such as about 10±0.1, is maintained. Precipitate is formed and is recovered by any suitable technique, e.g. centrifugation, filtration, etc. or combinations of these, and is then typically washed e.g. with distilled water to achieve a neutral pH, and dried.

The Cu-LDH materials are then calcined by any suitable method. In some aspects, this is accomplished e.g. in air at a temperature ranging from about 400 to 800° C., such as for about 400, 500, 600, 700, or 800° C. Calcination is allowed to proceed for a period of time suitable to obtain the desired level of decomposition, such a from about 6 to 10 hours, e.g. about 6, 7, 8, 9, or 10 hours.

The resulting products are ready for use upon cooling.

Reactions that are Catalyzed by the Catalysts

The catalysts disclosed herein may be used to catalyst any reaction that is amendable to catalysis by a CuMgAl catalyst (for CuMgAlI and CuMgAlII). Examples include but are not limited to: C—C coupling reactions like Ullmann reaction, aza-Michael addition, Aldol condensation, Suzuki coupling, and 1,3-dipolar cycloaddition reactions.

In some aspects, the reaction is the Henry reaction. When the reaction is a Henry reaction, the method that is used can be a conventional Henry reaction (e.g. heating a mixture of 4-nitrobenzaldehyde, nitromethane and catalyst together at a temperature ranging from e.g. about 80 to about 100° C., such as about 90° C., until completion.

However, in preferred aspects, the reactions, including the Henry reaction, are performed via an ultrasound method. In this method, heating is generally not necessary, and the reaction is typically performed at a temperature in the range of from about 25-30° C., such as about 25, 26, 27, 28, 29 or 30° C. During the reaction period (typically at least about 30 minutes, such as about 30, 40, 50, 60, 70, 80, 90, 100 or 110 minutes, or 2 hours or more) the reactants are exposed to ultrasound energy/radiation. This may be accomplished e.g. by placing a reaction vessel containing reactants in an ultrasonicator bath. Reaction products are ultimately recovered e.g. by extraction in a suitable solvent, evaporation, crystallization, etc. as needed to achieve recovery.

In some aspects, the products are pure crude β-nitro-alcohols. Thus, the present disclosure also encompasses methods of making a β-nitro-alcohol, comprising combining 4-nitrobenzaldehyde, nitromethane and a catalyst as described herein in a reaction vessel and exposing the reaction vessel to ultrasonic energy for a period of time sufficient to convert the 4-nitrobenzaldehyde and nitromethane to one or more β-nitro-alcohols. It is noted that the reactions take place with, in some cases, 100% atom economy. In some aspects, the catalyst that is used is the CuMgAl-I catalyst. As such, the CuMgAl-I catalyst can be considered a suitable efficient (100% atom economy) catalyst for the selective synthesis of nitro alcohol.

Product yields are typically very high, e.g. in the range of about 50 to 100%, and usually about 50, 55, 60, 65, 70, 75, 80, 85, 90, 95 or 100%.

Recycling the Catalysts

The results presented in the Examples section below showed that there was no apparent decline in the catalytic activity of the catalysts, even after six runs. Thus, the disclosed catalysts are "recyclable" in that after they are used to catalyze one reaction (e.g. a first reaction, they can be recovered and used to catalyze another or a plurality of other reactions (e.g. second, third, fourth, fifth, sixth, etc. reactions).

Recovery of the solid catalyst is generally straightforward and is accomplished e.g. by filtration, although other means (e.g. centrifugation) are not excluded. Once the solid is recovered, it is generally washed with a suitable solvent (e.g. acetone, an alcohol such as methanol or ethanol, etc.) to remove excess reactants and/or products from the first or previous reaction, and is then usually dried before reuse.

Without being bound by theory, it is believed that the excellent catalytic performance of e.g. the CuMgAl-I (Cu/Mg/Al=1:1:1) catalyst is due to the combined effects of nanosized crystallites with a large surface area, mesoporosity, and superior basic properties, which provide a durable sustainable catalyst that can be reused over a long period of time. For example, the catalysts can typically be reused at least about 5-50 times, such as about 5, 10, 20, 25, 30, 35, 40, 45 or 50 times, without diminished catalytic activity. In other words, the steps of the synthesis methods described herein can be repeated multiple times using the same batch or sample of catalyst, provided the catalyst is recovered, washed and (optionally dried) before it is reused. This makes the catalysts suitable for use in automated, high throughput syntheses.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example

1. Introduction

Great progress has been made in the development of mesoporous solid bases in the last decade.[10] They are extremely desirable in green catalytic processes owing to their advantages, including accelerated mass transfer, negligible corrosion, and easy separation. In addition to their widespread applications in the catalytic synthesis of biologically active organic molecules and fine chemicals, mesoporous solid bases have also been used as catalysts in the field of energy and environmental research.[11] Nanosized metal oxides behave efficiently as they have unique features such as high specific surface area, electric conductivity, and thermal stability. The utilization of nanosized mesoporous solid-base catalysts is an alternative to the classical environmentally unfriendly homogeneous catalysts. Metal oxides synthesized from hydrotalcite-like structures are considered as nanosized mesoporous solid-base catalysts, which have unique features with respect to crystallite size, morphology, and surface area, as well as high catalytic efficiency in various catalytic reactions.[12,13,14,15] Ultrasound irradiation has been proven to be an important tool in the arsenal of "green chemistry."[16-18] The utilization of ultrasound irradiation is commonly termed "sonochemistry."

In the present work, three nanosized mesoporous CuO/MgAlOx catalysts, CuMgAl-I, CuMgAl-II, and CuMgAl-III, have been prepared from CuMgAl-layered double hydroxides, CuLDH-I, CuLDH-II, and CuLDH-III catalysts were employed for the Henry reaction between nitromethane and a variety of benzaldehydes assisted by ultrasound irradiation. The aim of this study was to synthesize alcohols with 100% atom economy and high turnover frequencies (TOFs). A thorough characterization of catalysts was also performed to understand the relationship between the physicochemical properties of the catalysts and their catalytic functionality.

2. Results and Discussion 2.1. Chemical Composition by Inductively Coupled Plasma Atomic Emission Spectroscopy (ICP-AES).

The ICP-AES analysis of the Cu-LDH precursor samples was carried out to determine their chemical composition. The Cu/Mg/Al molar ratios in the three solids are presented in Table 1 and are very close to the molar compositions used in the synthesis of the CuMgAl-layered double hydroxides. These results confirm the efficacy of the preparation procedure used in the present work.

TABLE 1

Chemical Composition of As-Synthesized Cu-LDH Precursors

|  | CuLDH-I | CuLDH-II | CuLDH-III |
|---|---|---|---|
| Cu/Al | 0.95 | 1.40 | 1.90 |
| Mg/Al | 0.97 | 0.57 |  |
| Cu + Mg/Al | 1.92 | 1.96 | 1.88 |

2.2. X-Ray Diffraction (XRD)

The powder XRD patterns of the as-synthesized CuLDH precursor samples are shown in FIG. 1A. The diffraction patterns reveal the typical crystalline phase of a carbonate-containing layered double hydroxide phase (JCPDS 22-700).[19] The powder XRD (PXRD) patterns of three samples show sharp and intense diffraction peaks at $2\theta=11$, 23, and 34° corresponding to (003), (006), and (009) reflections and broad diffraction peaks at $2\theta=39$, 47, and 56° associated with (015) and (018) reflections, respectively. However, a poorly crystalline malachite phase [$Cu_2(OH)_2CO_3$, JCPDS 10-0399] was also detected in the PXRD pattern of the CuLDH-III sample, which is mainly due to the high copper content in the material. FIG. 1B shows the PXRD patterns of the CuLDH samples calcined at 500° C. for 8 h. The formation of metal oxide of the predominant metallic cation was observed after thermal decomposition of layered double hydroxide below 700° C.[20] In the case of CuMgAl-I and CuMgAl-II samples, crystalline CuO phase (JCPD 01-078-0428) was observed along with the MgO periclase structure. Upon calcination, the CuMgAl-III sample, which is composed of the layered double hydroxide and malachite phases, yielded highly crystalline CuO and poorly crystalline $\gamma$-$Al_2O_3$ phases.[21] The formation of CuO phase at low temperature can be ascribed to the well-known Jahn-Teller effect of copper ions[22] and their behavior inside brucite-like layers.[23] The crystallite size of the CuO phase, determined by using the Debye-Scherrer equation, was calculated to be around 18, 21, and 25 nm for CuMgAl-I, CuMgAl-II, and CuMgAl-III samples, respectively. The gradual increase in CuO crystallite size can be attributed to the precipitation of copper particles within the LDH layers resulting in grain growth of platelets of the Cu-LDH samples,[24] which in turn results in the formation of highly crystalline CuO phase after calcination in air at 500° C. Relatively intense XRD reflections due to $\gamma$-$Al_2O_3$ appeared in the CuMgAl-III sample, while CuMgAl-I and CuMgAl-II samples have not shown these reflections. This is mainly due to the Cu, Mg, and Al composition of the samples. The Cu/Mg/Al ratio for CuMgAl-III is 2:0:1, while it is 1:1:1 and 1.5:0.5:1 for CuMgAl-I and CuMgAl-II samples, respectively. The CuMgAl-III sample does not contain any Mg; it contains only Cu and Al. The absence of Mg in the CuMgAl-III sample could be the reason for the dominance of $\gamma$-$Al_2O_3$ reflections. It is also well known that $Al_2O_3$ is present in the $\gamma$ phase structure at a relatively low temperature.[25] The presence of MgO could suppress the formation of well-crystalline $Al_2O_3$ phase, which could be attributed to the more dominant appearance of the periclase structure than the amorphous-like structure of $Al_2O_3$ at 500° C.

2.3. Morphology Studies by Scanning Electron Microscopy (SEM) and High-Resolution Transmission Electron Microscopy (HRTEM)

The SEM images for the dried Cu-LDH precursors and calcined CuMgAl ternary oxide samples were obtained (not shown). The SEM images of the LDH precursor samples clearly revealed that the LDH precursor materials formed platelike agglomerated particles. The morphology of the LDH material was changed with an increase of Cu content or a decrease of the Mg content in LDH precursors. Most of the particles in the CuMgAl-III sample lost the best-defined platelet structure, and the platelet size decreased upon an increase of Cu inclusion. The calcined CuMgAl-I sample is composed of aggregated nanoparticles with undefined spongelike morphology. The morphology of the CuMgAl-II sample is very similar to that of the CuMgAl-I sample; however, relatively large particles were formed in this sample. In contrast, the CuMgAl-III sample shows individual isolated near-spherical-shaped aggregated particles with a larger size (approximately 2 μm) than in the other two samples. It is known that the decarbonation process that takes place during the calcination of the hydrotalcite samples is an exothermic process.[26] The destruction of the LDH layer structure to form Mg—Al oxides and the expulsion of copper oxide particles precipitated within the layered structure resulted in the formation of macropores. The growth of large particles of the CuLDH-III sample, which in turn resulted in the highly crystalline CuO phase after calcination is majorly due to high copper loading. These results are in accordance with the XRD data. The EDX profiles of the CuMgAl catalysts were obtained (not shown). The chemical compositions are shown in Table 2.

TABLE 2

Bulk (EDX) and surface (XPS) elemental composition of CuMgAl ternary metal oxide catalysts

| Catalyst | Bulk elemental composition (atom. %) | | | Surface elemental composition (atom %) | | |
|---|---|---|---|---|---|---|
|  | Cu | Mg | Al | Cu | Mg | Al |
| CuMgAl-I | 30.07 | 10.70 | 14.05 | 30.67 | 10.55 | 15.01 |
| CuMgAl-II | 44.54 | 5.99 | 14.12 | 40.11 | 5.58- | 16.11 |
| CuMgAl-III | 58.32 | 0.03 | 13.95 | 58.39 | — | 18.95 |

The CuMgAl-III sample has the highest Cu content compared to the other two samples, as anticipated.

The HRTEM images showed that the CuMgAl-I and CuMgAl-II samples (FIG. 2) are composed of small irregular sheets of Mg/Al/Cu oxides, which could be beneficial for a high exposure of active $Cu^{2+}$ sites. The two samples with sheetlike morphology have size ranging from 10.5 to 24.5 nm. Large sheet particles are likely due to Mg—Al—O, whereas smaller particles are CuO. In the HRTEM image of the CuMgAl-III sample, several small-size CuO nanoparticles are clearly visible, while large sheets of MgO disappeared. The images clearly exhibit that lattice fringes correspond to the "d" spacing of MgO and CuO. The HRTEM images of CuMgAl-I and CuMgAl-II samples exhibited particles with lattice fringes by a distance of 0.243 nm, which could be attributed to the (111) plane of the cubic MgO phase. The lattice fringes of CuO particles, which could be confirmed by the high crystalline nature with a d-spacing of 0.254 nm, belong to the lattice plane of (111).[27] The particle size distribution of CuO particles in the CuMgAl-III sample was calculated from the HRTEM results, and the average particle size is about 13-15 nm.

2.4. $N_2$ Physisorption Studies

The $N_2$ adsorption-desorption isotherms obtained at −196° C. for all of the calcined samples are shown in FIG. 3A. The CuMgAl-I sample exhibited type-IV isotherm with H4 hysteresis loop, which is characteristic of the presence of slit-like mesopores.[28] The CuMgAl-II and CuMgAl-III samples show type-II isotherms with a clear H3 hysteresis loop according to the IUPAC classification.[29] The H3 hysteresis loops exhibited a delayed condensation in the adsorption branch of the isotherm and showed no limiting adsorption at high P/P° values. The hysteresis loops differ depending on the extent of Cu/Mg substitution in the layered hydrotalcite sheets. The hysteresis loop of the CuMgAl-III sample, with Cu/Mg 2 is narrower than that of the CuMgAlII sample, with Cu/Mg 1, which indicates the possible precipitation of crystalline copper oxide particles with a different surface area and pore structure. The pore size distribution patterns for calcined CuMgAl ternary oxide samples were obtained from the adsorption branch of the isotherms by using the nonlocal density functional theory (NLDFT) method (FIG. 3B). A multimodal distribution in the micro-, meso-, and macrosizes was observed for CuMgAl-II and CuMgAl-III samples, whereas a bimodal distribution in the micro- and mesosizes is detected for the CuMgAl-I sample. The changes in the pore size distribution could be attributed to the different crystalline phases with different sizes. The results from Na adsorption-desorption measurements were consistent with SEM images). Table 3 shows the BET surface areas ($S_{BET}$), total pore volumes ($V_p$), and average pore sizes for all of the calcined samples. The CuMgAlI sample has a higher surface area and pore volume (78 $m^2\ g^{-1}$ and 0.210 $cm^3\ g^{-1}$) than the CuMgAl-II (70 $m^2\ g^{-1}$ and 0.194 $cm^3\ g^{-1}$) and CuMgAl-III (20 $m^2\ g^{-1}$ and 0.153 $cm^3\ g^{-1}$) samples. The notable decrease in the surface area with increasing copper concentration is linked to an increase in the particle sizes of the materials, as demonstrated by XRD and SEM analyses.

TABLE 3

BET Surface Areas, Total Pore Volume, and Pore Sizes Derived from the $N_2$ Physisorption Data of the CuMgAl Samples

| Sample | $S_{BET}$ ($m^2\ g^{-1}$) | pore volume ($cm^3\ g^{-1}$) | half pore width (Å) |
|---|---|---|---|
| CuMgAl-I | 78 | 0.210 | 16 |
| CuMgAl-II | 70 | 0.194 | 14 |
| CuMgAl-III | 20 | 0.153 | 19 |

2.5. X-Ray Photoelectron Spectroscopy (XPS)

Figure 4A:
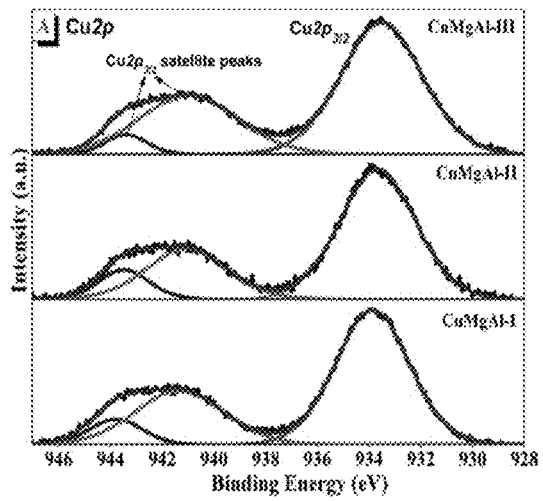
FIG. 4A-D. XPS core spectra of (A) Cu 2p (B) Mg 2p (C) Al 2p, and (D) 0 is for calcined CuMgAl samples.
Figure 4B:
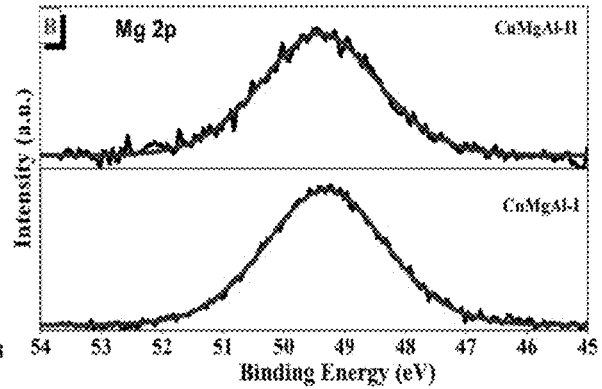
Figure 4C:
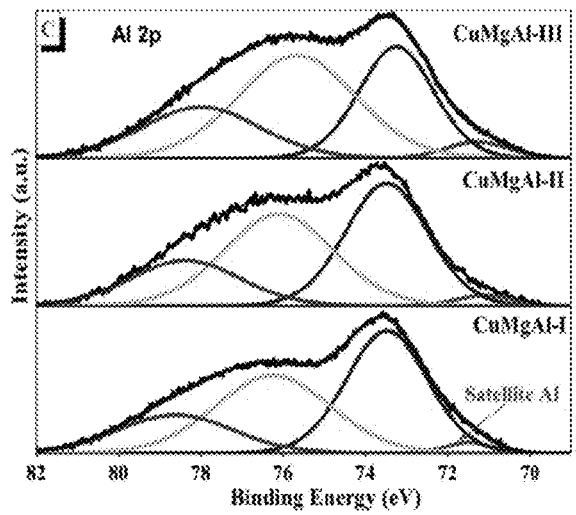
Figure 4D:
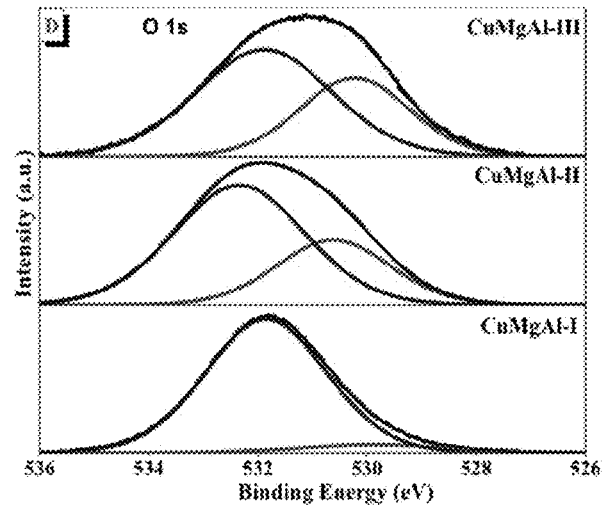

To gain an insight into the location and nature of the Cu, Mg, Al, and O species present in CuMgAl samples, XPS studies were performed. The deconvoluted XPS spectra of the Cu 2p, Mg 2p, Al 2p, and O 1s core levels are shown in FIG. 4A-D. The deconvoluted Cu $2p_{3/2}$ X-ray photoelectron spectra for the CuMgAl-I, CuMgAl-II, and CuMgAl-III samples are shown in FIG. 4A. The Cu $2p_{3/2}$ peak position in the range of 933.5-933.9 eV and shape of the Cu $2p_{3/2}$ spectral lines are consistent with the presence of CuII in the form of CuO phase.[30-32] The assignment of binding energy is also corroborated by the presence of the satellite signals at 942.2 and 943.9 eV, which are characteristic of CuII species. The CuLMM Auger spectra for CuMgAl ternary oxide samples were obtained (not shown). A minor difference was observed in the kinetic energy maximum of CuLMM Auger photoelectron spectra of the samples. The CuMgAl-I sample showed a kinetic energy maximum at 917.3 eV, and an increase in the Cu content resulted in an increase of the kinetic energy (CuMgAl-II: 917.5 eV, CuMgAl-III: 917.9 eV). Diaz-Droguett et al.[33] reported that $Cu^{2+}$ species have a kinetic energy of the Auger transition at ca. 917-918 eV. These observations indicate that the three samples possessed $Cu^{2+}$ species, and the shift in kinetic energy maximum is most likely due to the difference in interaction between the CuO and other oxides.

The binding energy of the Mg 2p peak (FIG. 4B) appeared around 49.3 eV for both CuMgAl-I and CuMgAl-II samples; the positions of the peaks are in accordance with the peak of XPs for $Mg^{2+}$ in MgO phase. Similarly, the samples exhibited three different XP peaks of Al 2p at 73.2, 75.7, and 78.4 eV corresponding to the species in the $Al^{3+}$ oxidation state. The observed results confirm that the Cu, Mg, and Al atoms are in bonding with oxygen atoms as they remained clustered during the thermal treatment, and these oxides might exist in the amorphous state or very small crystallites. The existence of a combination between Mg, Al, and Cu and oxygen atoms is also proved by the O 1s spectra shown in FIG. 4D. The O 1s spectra of the samples showed two peaks; the peak at 530.4 eV could be attributed to the lattice oxygen of Mg—O, Cu—O, and Al—O species,[34] while the second peak at 531.8 eV could be associated with the oxygen-adsorbed species, surface hydroxyl, or adsorbed water molecules.[35] The ratio of the two peak intensities indicates that an increase of the Cu content in LDH resulted in an increase of more surface oxygen-adsorbed species. The decline in the intensity of the peaks of XPS detected with an increase of the Cu content (principally Mg 2p and O 1s) indicates the greater homogeneity of Cu species on the surface. The bulk atomic composition of materials (based on the precursor amounts) is in accordance with the surface atomic composition.

2.6. Fourier Transform Infrared (FT-IR) Spectroscopy

Figure 5:
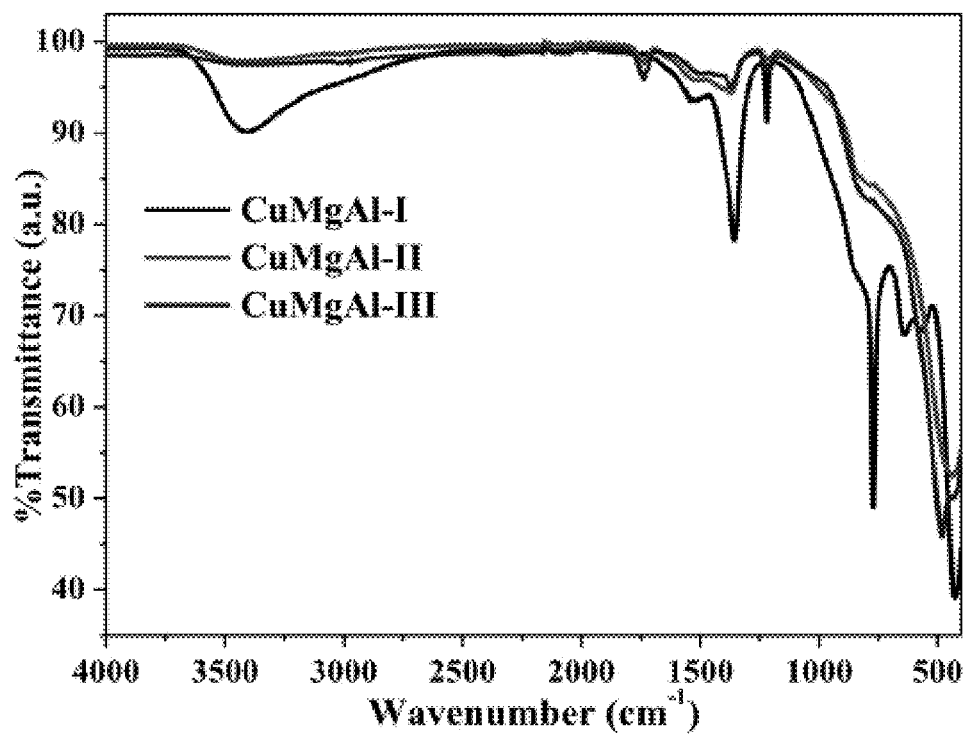
FIG. 5. FT-IR spectra of CuMgAl-I, CuMgAl-II, and CuMgAl-III samples.

FT-IR spectroscopy was used further as a tool to investigate the structural feature of the synthesized CuO/MgAlOx catalysts (FIG. 5). A broad band at 3420 $cm^{-1}$ could be attributed to the O—H vibration of the structural —OH groups. It is interesting to observe a band at 1358 $cm^{-1}$, with a shoulder at 1530 $cm^{-1}$, due to the presence of $[CO_3]^{2-}$ species.[36] The FT-IR bands in the 500-1000 $cm^{-1}$ region could be assigned to M-O and M-OH species. It was reported that vibrations due to Cu—O appears around 530 and 590 $cm^{-1}$.[37] And Cu—OH species show bands at 469 and 720 $cm^{-1}$.[38] Hsu and Nacu reported a wide, strong absorption band at 430 $cm^{-1}$ for the stretching vibration of Mg—O.[39] It is interesting to note the γ-$Al_2O_3$ phase yields IR absorption bands around 759, 630, 652, 617, 554, and 465 cm$^{-1}$.[40] From all of these observations, it is possible to argue that the FT-IR bands observed at 850, 780, 630, and 430 cm$^{-1}$ in the samples are due to lattice vibrations involving the Mg$^{2+}$, Cu$^{2+}$, and Al$^{3+}$ cations. It is also interesting to note that the intensity of the observed bands is strikingly high in the case of the CuMgAl-I sample compared to other two samples. An increase in the IR peak intensity is usually related to an increase in the amount (per unit volume) of the functional group associated with the molecular bond. A change in intensity could also be due to some changes corresponding to the sample composition related to the bonds, phase, crystallinity, etc. The synthesized samples clearly possessed different phases with different elemental compositions and sizes of the particles. The CuMgAl-I sample majorly contained nanosized crystalline MgO and CuO phases. This could be the major reason for the appearance of high-intense FT-IR bands corresponding to the M-O and M-OH species in this sample.

2.7. $CO_2$ Temperature-Programmed Desorption ($CO_2$-TPD)

Figures 6A, 6B, 6C:
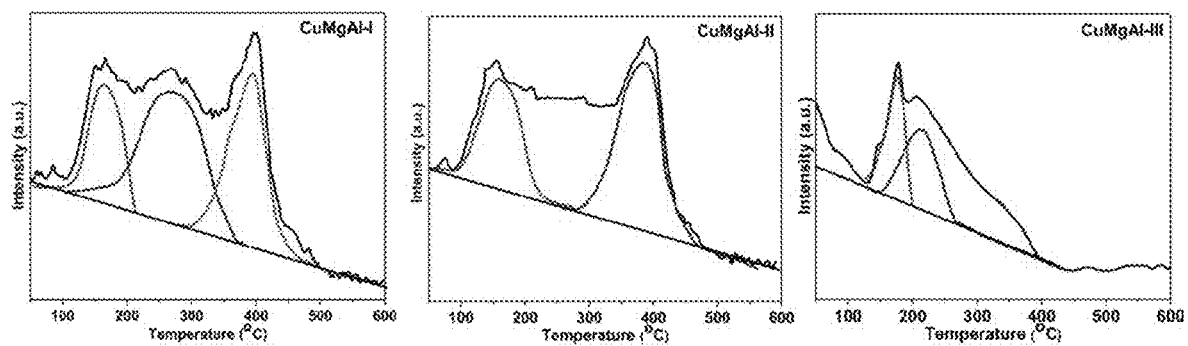
FIG. 6A-C. $CO_2$-TPD profiles of the (A) CuMgAl-I, (B) CuMgAl-II, and (C) CuMgAl-III samples.

The deconvoluted $CO_2$ desorption profiles for the CuMgAl-I, CuMgAl-II, and CuMgAl-III samples are shown in FIG. 6. It is generally accepted that weakly basic sites are correlated with OH structural groups (Brønsted basic sites), moderate basic sites are attributed to the metal-oxygen pairs in Mg—O (Lewis basic sites), and strong basic sites are associated with low-coordination oxygen atoms.[41] The total number of basic sites, which are ascribed to the presence of —OH and Mg—O groups, decreased monotonically as the Cu content increased (FT-IR spectra). As shown in FIG. 6, the CuMgAlI sample exhibited three desorption peaks corresponding to weak, medium, and strong basic sites. The CuMgAl-II sample showed two peaks attributed to weak and strong basic sites. In contrast, relatively small desorption peaks centered at 150 and 200° C. (due to weak basic sites) were observed in the case of the CuMgAl-III sample. The quantitative data from the TPDCO$_2$ experiments were obtained to understand the number of basic sites. It is known that the presence of MgO increases the quantity of the basic sites, especially the medium-strength basic sites.[42] The CuMgAl-III sample possessed fewer basic sites (86.3 mmol g$^{-1}$) compared to CuMgAl-II (220.5 mmol g$^{-1}$) and CuMgAl-I (292 mmol g$^{-1}$). The high surface area, presence of copper oxide species, and increase in the basicity in the CuMgAl-I catalyst could offer better catalyst activity in the Henry reaction.

2.8. Activity of Catalysts in the Henry Reaction

The Henry reaction is a base-catalyzed C—C bond-forming reaction between nitroalkanes and aldehydes or ketones (Scheme 1).

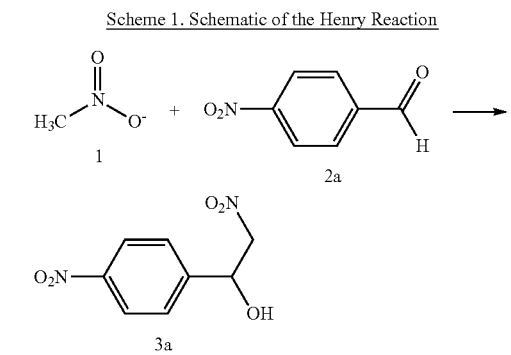

Scheme 1. Schematic of the Henry Reaction

Therefore, the catalytic efficacies of CuMgAl-I, CuMgAl-II, and CuMgAl-III samples were investigated for this reaction. For comparison purposes, the catalytic activities of the bulk oxides (MgO, γ-Al$_2$O$_3$, and CuO) were also tested. The reaction between nitromethane (1) and 4-nitrobenzaldehyde (2a) in the presence of catalyst was carried out under solvent-free conditions using conventional heating and ultrasound irradiation. In each reaction, the same product, 1-(4-nitrophenyl)-2-nitroethan-1-ol (3a), was obtained (as determined by thin layer chromatography (TLC)). The structure of the product 3a was elucidated by spectroscopic and analytical methods. The IR spectrum of 3a shows a band at 3447.02 cm$^{-1}$ which is a characteristic band for the alcoholic OH group, and two bands at 1514.35 and 1339.51 cm-1 attributed to the presence of the NO$_2$ group. The $^1$H NMR spectrum shows a broad singlet at δ=5.65 ppm, which is a characteristic of proton of —OH groups, which disappeared upon addition of D$_2$O. The aliphatic protons appear as a multiplet at δ=4.48 ppm for 1-H and as a pair of multiplets at δ=4.60 and 4.85 ppm for 2-H protons. Additionally, the signals of the aromatic protons appear in the aromatic region of the spectrum. The $^{13}$C NMR spectrum shows two aliphatic saturated carbon atoms at δ=128.70 and 69.98 ppm for C-2 and C-1, respectively. The results obtained from the catalytic test reactions are presented in Table 4.

TABLE 4

Catalytic Test Reaction of 1 and 2a Performed Under Conventional and Ultrasound Irradiation Condition

| Catalyst | Conventional method | | Ultrasound method | | Product structure (3a) |
|---|---|---|---|---|---|
| | Time (min.) | Yield (%) | Time (min.) | Yield (%) | |
| CuMgAl-I | 30 | 86 | 1 | 99 | (structure shown) |
| CuMgAl-II | 45 | 75 | 3 | 98 | |
| CuMgAL-III | 65 | 71 | 5 | 92 | |
| MgO | 90 | 38 | 30 | 45 | |
| γ-Al$_2$O$_3$ | 90 | 0 | 30 | 3 | |
| CuO | 90 | 0 | 30 | 5 | |

The performances of all the catalysts were studied by monitoring the formation of the product 3a. The target product was formed with 100% conversion of reactants in the case of CuMgAl catalysts; however, the yield of the catalysts differed considerably (Table 4). The data in Table 4 show that all of the CuMgAl catalysts offered acceptable yields of the product. Among the bulk oxides, MgO exhibited considerable yield, but other two oxides CuO and γ-$Al_2O_3$ have not shown any conversion under the studied reaction conditions. The ultrasonic-assisted catalytic reactions were completed in shorter reaction times with higher yields of the product compared to the reactions carried out by the conventional heating method. A discrepancy in the catalytic performance of the catalysts existed as CuMgAl-I required only 30 min to obtain 86% yield, whereas CuMgAl-II and CuMgAl-III needed 45 and 65 min to obtain 75 and 71%, respectively, under conventional heating. The CuMgAl-I catalyst offered a high turnover frequency in the Henry reaction due to the presence of more basic sites. However, under ultrasonic irradiation, the difference in activity between CuMgAl-I and CuMgAl-II is small, which is probably due to the fact that these two samples possessed majorly CuO and MgO phases. The synergy between the copper species and surface Lewis basic sites derived from MgO presented in the samples is responsible for the nucleophilic activity at the oxygen atom. In addition, the physical phenomenon known as acoustic cavitation at the solid-liquid interface under ultrasonic irradiation is suggested to enhance the activity of a catalyst.[43] And this effect might be equally contributing to improve the activity of both CuMgAl-I and CuMgAl-II catalysts in the Henry reaction. It has been suggested that the microjet impact and shock wave damage at the surface of a solid (catalyst), along with the shock wave associated with the cavitation collapse, cause localized deformation and surface erosion, which increases the size of the possible reaction area.[44] It is noteworthy that the intensity of cavitation depends on the type of solvent and frequency of ultrasonic waves used for the reaction. Therefore, the solvent used to perform the ultrasonic assisted reaction must be carefully chosen. As a general rule, most reactions are performed in water; however, in this methodology, nitromethane was used as a solvent. It was found that nitromethane has a slightly high vapor pressure than water[45] and cavitation is more difficult with a low-vapor pressure liquid. Recent advances in green chemistry principles drive chemists to strive to achieve maximum yield and also design a methodology that maximizes the incorporation of atoms of the reactants into the desired product (atom economy) to make reactions greener. In this context, the determination of the atom economy is important. The atom economies for the investigated catalysts in the Henry reaction were calculated by eq 146 atom economy mass of atoms of the desired product mass of atoms of the reactants 100=x (1). It was observed that the atom economy for the reaction with CuMgAl-I (i.e., under the best conditions) to give compound 3a is 100%. CuMgAl-I is the most efficient catalyst for the synthesis of 2-nitro-1-(4-nitrophenyl) ethanol (3a) because it offered the highest yields (99 and 86%) in the shortest reaction times under both ultrasonic and conventional methods, respectively. Therefore, CuMgAl-I was selected to explore the substrate scope of the Henry reaction under ultrasound irradiation conditions; the results are summarized in Table 5.

TABLE 5

Scope and Generality of the Henry Reaction Under Optimum Reaction Conditions

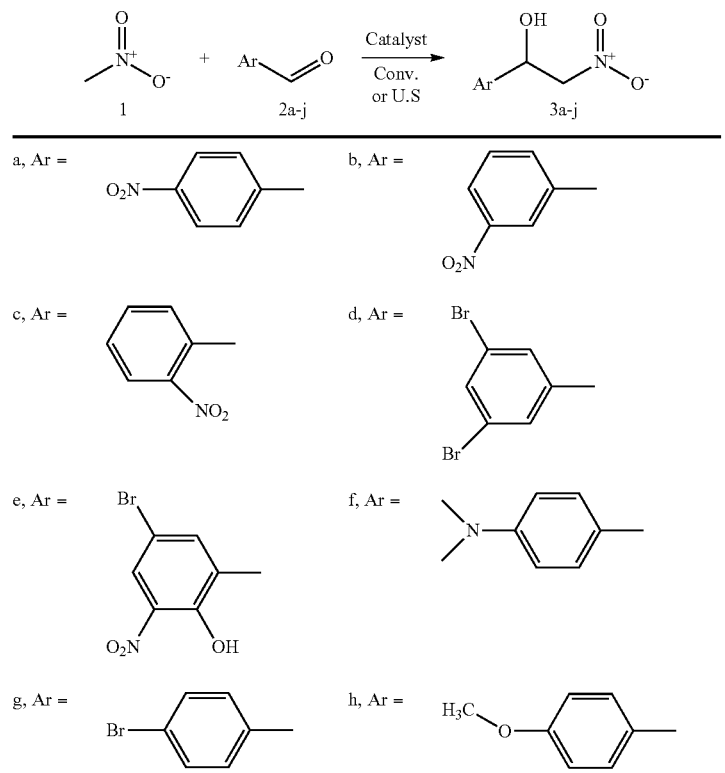

TABLE 5-continued

Scope and Generality of the Henry Reaction Under Optimum Reaction Conditions

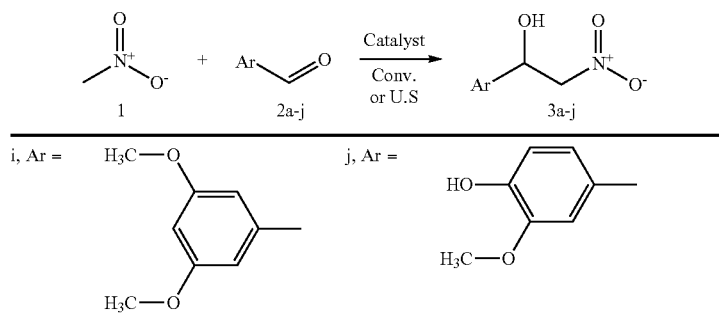

The structures of the isolated products 3a-j were elucidated by IR, $^1$H, and $^{13}$C NMR spectroscopy techniques. The IR spectra show a characteristic band for the OH groups of the products 3a-j. It is clear from the data in Tables 4 and 5 that the CuMgAl-I catalyst displays efficient activity in all of the reactions, giving high yields in short reaction times (1-14 min). Furthermore, only one isolable alcohol product was synthesized using the CuMgAl-I catalyst in the reactions between nitromethane and various aldehyde derivatives. The CuMgAl-I catalyst represents a mixture of nanosized CuO and MgO phases, as evidenced by the PXRD patterns. In addition, γ-$Al_2O_3$ is usually formed in an amorphous phase in the presence of CuO at a low calcination temperature of around 500° C.[14] The CuMgAl-I catalyst possessed a large surface area and pore volume compared to the other two synthesized catalysts (CuMgAl-II and CuMgAl-III). It is known that textural properties such as surface area and pore size have a significant impact on the catalyst performance. Results from $N_2$ physisorption measurements of samples indicated that a multimodal distribution in the micro-, meso-, and macrosizes was presented in CuMgAl-II and CuMgAl-III samples, whereas a bimodal distribution in the micro- and mesosizes is detected for the CuMgAl-I sample. It was also known that smaller or larger pores are not suitable for the catalysis, as larger pores could cause the formation of larger CuO crystallite and decrease its dispersion. The smaller pore size in the catalysts could cause diffusional limitations. Due to the moderate particle size and pore size, CuMgAl-I could offer better performance. The superior catalytic activity of the CuMgAl-I sample could be attributed to the combination of synergistic effects between the physicochemical properties of the catalysts and ultrasonic irradiation. It is also well known that the presence of MgO and —OH groups in the catalysts is responsible for the Lewis and Brønsted basic sites, respectively.[47] The nitroaldol reaction (Henry reaction) is usually carried out by adding small amounts of bases such anionic bases, alkali-metal hydroxides, alkoxides, carbonates, and sources of fluoride anion (e.g., TBAF) or nonionic organic amine. It was previously reported that the type of the base and solvent used do not have a significant effect on the overall result of the reaction.[48] However, the presence of a strong alkali such as aqueous NaOH could lead to the dehydration of the nitro alcohol products to give nitroalkenes.[49] In the present system, MgO acts as a base and γ-$Al_2O_3$ acts as a moderate acidic site due to the $Al^{3+}$ cation, and the $Cu^{2+}$ species are widely accepted as an active species in the Henry reaction. Therefore, the dehydration of the nitro alcohol products could be ruled out in the studied methodology and the catalytic selectivity toward alcohol formation is directly related to the dispersed copper sites. The synergy between the copper species and surface Lewis basic sites derived from MgO presented in the samples led to the nucleophilic activity at the oxygen atom, thus improving the activity for the Henry reaction. The TON and TOF values were calculated and are presented in Table 6. Remarkably, high TON and TOF values were achieved with a small amount of copper in the CuMgAl-I catalyst. On the basis of the observed catalytic activity results, the synthesized CuMgAl-I catalyst can be considered to be a suitable efficient catalyst for the selective synthesis of nitro alcohol.

TABLE 6

Henry Reaction Products Obtained from Different Aldehydes and Nitromethane Using CuMgAl-I Catalyst under Ultrasonic Irradiation

| Compound | Reactants | Henry Product Structure | Yield % | Time min. | TON | TOF $h^{-1}$ |
|---|---|---|---|---|---|---|
| 3a | 1, 2a | $O_2N$-C₆H₄-CH(OH)-CH₂-$NO_2$ | 99 | 1 | 12694 | 212 |

TABLE 6-continued

Henry Reaction Products Obtained from Different Aldehydes and Nitromethane Using CuMgAl-I Catalyst under Ultrasonic Irradiation

| Compound | Reactants | Henry Product Structure | Yield % | Time min. | TON | TOF $h^{-1}$ |
|---|---|---|---|---|---|---|
| 3b | 1, 2b | (3-nitrophenyl CH(OH)CH$_2$NO$_2$) | 99 | 1 | 12694 | 212 |
| 3c | 1, 2c | (2-nitrophenyl CH(OH)CH$_2$NO$_2$) | 99 | 1 | 12694 | 212 |
| 3d | 1, 2d | (3,5-dibromophenyl CH(OH)CH$_2$NO$_2$) | 99 | 3 | 12694 | 71 |
| 3e | 1, 2e | (5-bromo-3-nitro-2-hydroxyphenyl CH(OH)CH$_2$NO$_2$) | 95 | 7 | 12195 | 29 |
| 3f | 1, 2f | (4-dimethylaminophenyl CH(OH)CH$_2$NO$_2$) | 82 | 3 | 10526 | 58 |
| 3g | 1, 2g | (4-bromophenyl CH(OH)CH$_2$NO$_2$) | 96 | 1 | 12323 | 205 |
| 3h | 1, 2h | (4-methoxyphenyl CH(OH)CH$_2$NO$_2$) | 95 | 14 | 12195 | 15 |
| 3i | 1, 2i | (3,5-dimethoxyphenyl CH(OH)CH$_2$NO$_2$) | 82 | 7 | 10526 | 25 |
| 3j | 1, 2j | (4-hydroxy-3-methoxyphenyl CH(OH)CH$_2$NO$_2$) | 89 | 3 | 11424 | 63 |

2.8.1. Recycling of the Catalyst

Figure 7:
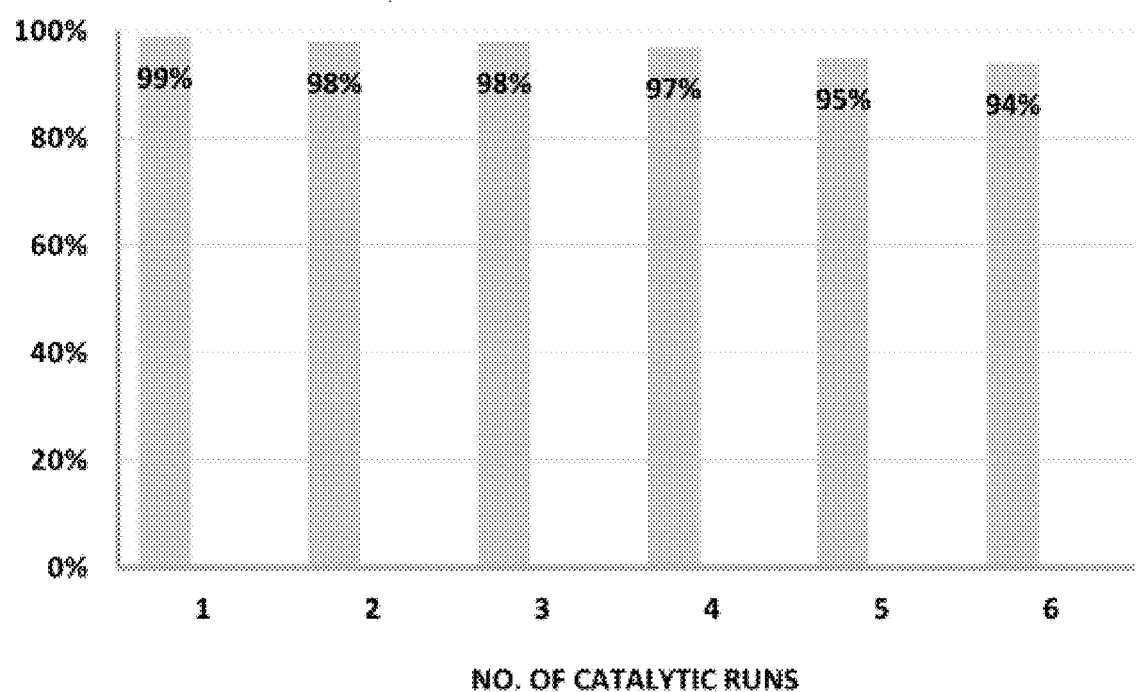
FIG. 7. Recycling of the CuMgAl-I catalyst in the reaction between 1 and 2c.

It was vitally important to study the stability of the CuMgAl-I catalyst under ultrasound conditions. Therefore, the reaction between 1 and 2c was repeated six times using a recovered catalyst. To recover the solid catalyst, it was filtered and washed with acetone after each catalytic cycle and then dried in vacuum before reuse. The catalytic activity was monitored for each reaction, and the results are presented in FIG. 7. The results showed that there was no apparent decline in the catalytic activity even after six runs, with the yields obtained in the recyclability test being within experimental error. As described previously, the superior catalyst performance under ultrasound irradiation may be due to the microjet impact and shock wave damage occurring on the catalyst surface. HRTEM analysis was used to study the effect of ultrasonic irradiation on the catalyst surface. The HRTEM image (not shown) of the spent CuMgAl-I sample showed the presence of agglomerated particles with very few lattice fringes, indicating that the ultrasonic waves caused localized deformation, and surface erosion resulted in an increased available interface for the reactions. Therefore, the HRTEM analysis of the spent catalyst provided evidence for enhanced TOFs in the Henry reaction.

Figure 8:
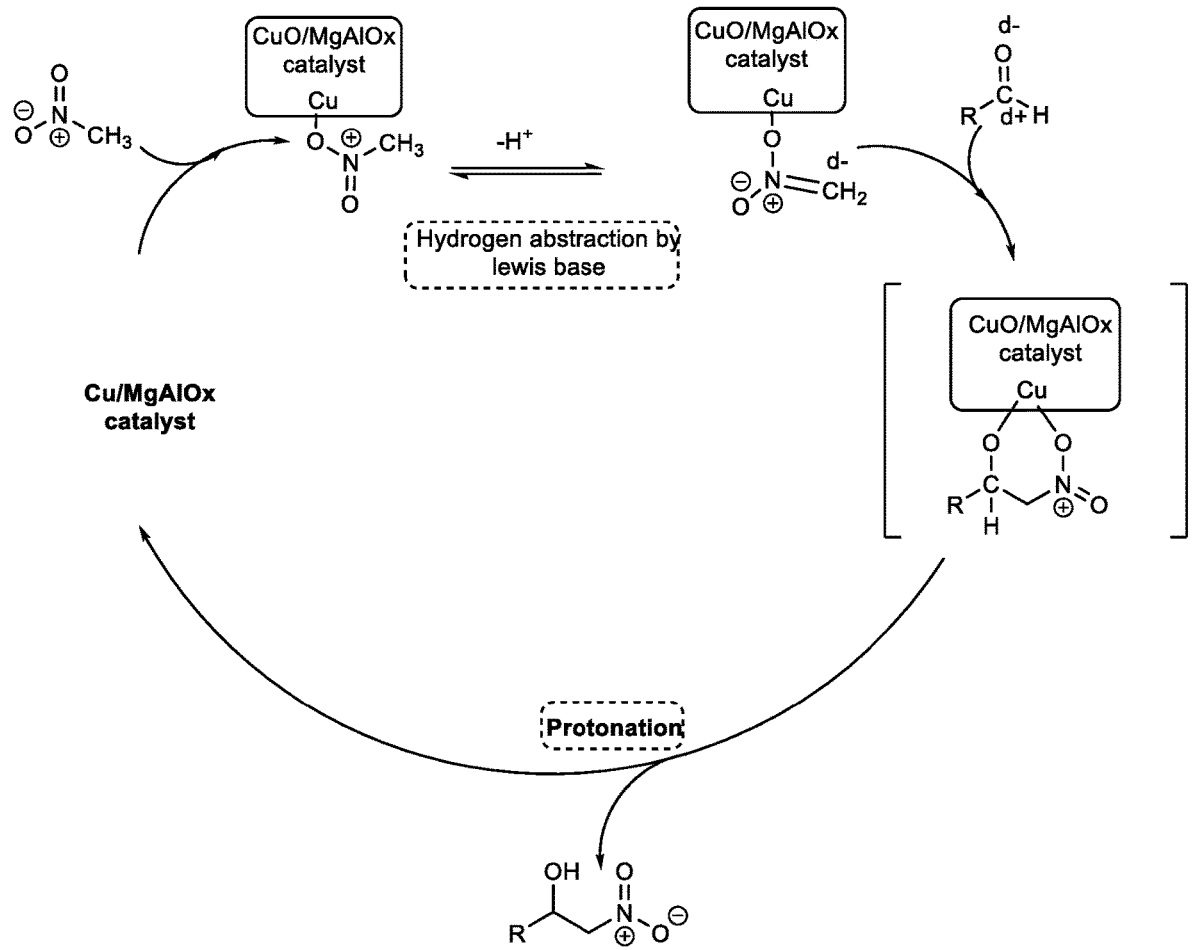
FIG. 8. Henry reaction mechanism over CuMgAl catalysts.

Based on the observed catalyst activity and characterization results, a proposed mechanism was developed for this reaction utilizing CuMgAl-I, CuMgAl-II, and CuMgAl-III catalysts. From the FT-IR and $CO_2$-TPD results, it is clear that CuMgAl-I and CuMgAl-II catalysts possess Lewis basic sites as well as OH-Bøonsted basic sites, while the CuMgAl-III catalyst does not possess any basic sites. Therefore, without being bound by theory, it appears that a plausible mechanism for the Henry reaction over synthesized CuMgAl catalysts can be based mainly on the copper active sites and Lewis base centers, as presented in FIG. 8. Initially, the nitromethane molecule is coordinated to the active Cu center on the surface of catalyst forming an intermediate. The hydrogen abstraction from the intermediate by the Lewis base sites yields the nitronate ion, and the nucleophilic carbon atom of the nitronate ion attacks the carbon of the carbonyl group in the aldehyde molecule to form β-nitro-alkoxide, as shown in FIG. 8. Finally, protonation of β-nitro-alkoxide affords β-nitro alcohol and catalyst, which are used for the next cycle.

3. Conclusions

The green reaction protocol described herein offers a rapid, atom-economic, and safe alternative to other methods for the Henry reaction to synthesize the nitro alcohol derivatives using the heterogeneous recyclable CuMgAl ternary oxide catalysts under ultrasonic irradiation. The CuMgAl ternary oxide catalysts were derived by the thermal decomposition of Cu:Mg:Al hydrotalcites with different Cu, Mg, and Al atomic ratios. The reactions were proceeded under mild reaction conditions and offered the products in excellent yields with 100% atom economy. The excellent catalytic activity could be attributed to the synergistic effect between the CuMgAl catalysts and ultrasonic irradiation. This remarkable synergistic effect between the ultrasound irradiation and the catalyst in the Henry reaction protocol was established according to the results obtained from HRTEM analysis of the used catalyst sample. The analysis showed that the presence of agglomerated particles with the cavitation collapse causes localized deformation and surface erosion enables an increase in the solid/liquid interface for the organic reactions. Other advantages of the present reaction protocol include simple separation and purification procedures. The excellent catalytic performance of the CuMgAl-I (Cu/Mg/Al=1:1:1) catalyst is due to the combined effects of nanosized crystallites with a large surface area, mesoporosity, and superior basic properties, which provide a durable sustainable catalyst that can be reused over a long period of time.

4. Experimental Section 4.1. Reagents. The following chemical reagents were used for the synthesis of the catalysts: aluminum nitrate nonahydrate, magnesium nitrate hexahydrate, sodium carbonate, and sodium hydroxide (all from Sigma-Aldrich Laborchemikalien GmbH, Seelze, Germany), copper(II) nitrate trihydrate (Fluka AG, Chemische Fabrik, CH-9470 Buchs, Switzerland), and distilled/deionized water. The following chemical reagents were used for the Henry reaction: nitromethane, p-nitrobenzaldehyde (all from BDH Limited, Poole, England), mnitrobenzaldehyde (Koch Light Research Laboratories, Gauteng, South Africa), o-nitrobenzaldehyde, p-bromo benzaldehyde, 4-dimethylaminobenzaldehyde, 5-bromo-3-nitrosalicylaldehyde, vanillin, 3,5-dimethoxy benzaldehde, 3,5-dibromobenzaldehde, and 4-methoxybenzaldehyde (all from Sigma-Aldrich Laborchemikalien GmbH, Seelze, Germany).

4.2. Synthesis of the Cu-LDHs. The copper/magnesium/aluminum layered double hydroxides (Cu-LDHs) were prepared by the co-precipitation method. Two solutions, namely, solution A, containing the calculated amounts of metal (Cu, Mg, and Al) nitrates, and solution B, containing the precipitating agents NaOH and $Na_2CO_3$, were added slowly and simultaneously by a peristatic pump to a flask containing distilled water at 50° C. to maintain the constant pH value (at around 10±0.1). The total contents were stirred by using an overhead stirrer to ensure rapid and efficient mixing to obtain the precipitate. The obtained precipitate was filtered through Whatmann5 filter paper, and the resulted cake was washed with distilled water until the residual solution pH became neutral.[44] The cake was then dried in an electric oven at 80° C. for 12 h. The theoretical Cu/Mg/Al ratios of the synthesized CuLDH materials are 1:1:1, 1.5:0.5:1, and 2:0:1 for Cu-LDHI, Cu-LDH-II, and Cu-LDH-III, respectively.

4.3. Synthesis of CuMgAl Catalysts. The as-synthesized Cu-LDH materials were calcined in a muffle furnace in a flow of air at 500° C. for 8 h to obtain CuMgAl catalysts. The solids obtained from Cu-LDH-I, Cu-LDH-II, and Cu-LDH-III were labeled as CuMgAl-I, CuMgAl-II, and CuMgAl-III, respectively.

4.4. Catalyst Characterization Methods. The chemical composition of the samples was determined using Optima 4300™ DV, PerkinElmer ICP-optical emission spectrometer. Powder X-ray diffraction (PXRD) studies were performed on all of the prepared solid samples by using a Bruker diffractometer (Bruker D8 advance target). The PXRD patterns were recorded with monochromatized Cu Kα irradiation (λ=1.5405 Å) at 40 kV and 40 mA. The different crystalline phases in each of the samples were identified by comparing the data with those compiled by the Joint Committee for Powder Diffraction Standards (JCPDS). The sizes of the crystallite phases were calculated by using the Scherrer equation: $D=K\lambda/\beta \cos\theta$, where "D" is the average crystallite size of the phase under investigation, "K" is the Scherrer constant (0.89), "λ" is the wavelength of the X-ray beam used (1.5405 Å), "β" is the full width at half-maximum (FWHM) of the diffraction peak, and "θ" is the diffraction angle. The X-ray photoelectron spectroscopy (XPS) measurements were carried out by using an X-ray photoelectron spectrometer (SPECS GmbH, Berlin, Germany) Prior to the analysis, the samples were degassed under vacuum inside the load lock for 16 h. The binding energy of the adventitious carbon (C 1s) line at 284.6 eV was used for calibration, and the positions of the other peaks were corrected according to the position of the C is signal. For the measurements of high-resolution spectra, the analyzer was set to the large-area lens mode with energy steps of 25 meV and in the Fixed Analyzer Transmission (FAT) mode with a pass energy of 34 eV and dwell time of 100 ms. A JEOL JSM840A scanning electron microscope and an FBI Tecnai F30 high-resolution transmission electron microscope were used to investigate the morphological characteristics of the solid samples. Prior to each measurement, the sample was placed on an aluminum block using carbon tape. The FT-IR spectra of the samples were obtained using a Bruker α-II FT-IR spectrometer. The $CO_2$-TPD analysis was performed using a CHEMBET-3000 instrument (Quantachrome). The samples were outgassed at 100° C. (1 h) by flowing helium gas over the sample. Then, the sample was saturated with $CO_2$ at 120° C. for 30 min. Subsequently, the sample was treated with helium gas to remove the physisorbed $CO_2$ gas. Finally, the TPD patterns of the samples were collected by ramping the sample temperature to 800° C. at a heating rate of 10° C. $min^{-1}$. $N_2$ physisorption experiments were carried out at −196° C. using a NOVA 3200 e automated gas sorption system (Quantachrome) to investigate the textural properties of the solids. Before every measurement, the adsorbent was pretreated at 150° C. for 6 h. The Brunauer-Emmett-Teller (BET) equation was applied to determine the specific surface areas, and the average pore radii were deduced from the equation $2Vp/SBET$, where Vp is the total pore volume (at P/P0=0.98).

4.5. Typical Procedure for the Henry Reaction.

4.5.1. Conventional Method. A mixture of 4-nitrobenzaldehyde (0.5 g), nitromethane (3 mL), and catalyst (150 mg) was heated together in a two-necked, round-bottom flask at 90° C. The progress of the reaction was monitored by TLC (eluent:diethyl ether/chloroform in 1:1). Upon completion of the reaction, the mixture was cooled and the product was extracted by dissolution in hot ethanol. The catalyst was removed by filtration and washed with alcohol prior to drying and reuse. After evaporation of the volatile materials under vacuum, compound 3a was recrystallized from EtOH/DMF.

4.5.2. Ultrasonic Method. A mixture of aldehyde 2a-j (3.3 mmol), nitromethane 1a (3 mL), and the catalyst (150 mg) was added to a three-neck, round-bottom flask, and the reaction mixture was subjected to ultrasound irradiation for the time required to complete the reaction (Table 1). All reactions were kept at 25-30° C.; the temperature was maintained by the addition and removal of water from the bath (the temperature inside the reaction vessel was 27° C., and the reaction flask was placed in the middle of the ultrasonicator bath to achieve effective cavitation). The progress of the reaction was monitored by TLC (eluent: diethyl ether/chloroform in 1:1). Then, the product mixture was cooled and extracted with acetone. The catalyst was then removed by filtration, and the products were purified by crystallization from EtOH/DMF to afford the pure crude β-nitro-alcohols 3a-j in excellent yields.

4.6. Characterization of the Reaction Products. All melting points were determined by using a Barnstead International 1002 melting point apparatus and are uncorrected. TLC was performed on aluminum silica gel 60 F254 (E-Merck). The spots were detected by UV light absorption. The IR spectra were recorded with a Thermo Nicolet™-6700 FT-IR spectrophotometer. $^1H$ and $^{13}C$ NMR spectra were recorded on a Bruker WM 400 spectrometer at 850 MHz in deuterated chloroform (CDCl) or dimethyl sulfoxide (DMSO-d6) using tetramethylsilane (TMS; 0.00 ppm) as internal standard. Chemical shifts (δ) are given in ppm relative to the signal for TMS as a standard, and coupling constants are given in hertz. The reactions performed under ultrasound irradiation were carried out in a Daihan (Wiseclean, D-40 MHz) ultrasonic bath.

4.7. Physical and Spectral Data of the Titled Compounds 3a-k. 2-Nitro-1-(4-nitrophenyl)ethan-1-ol (3a).

Mp 83-86° C. FTIR: vmax/cm-1 3447 (OH), 3114 (C—H), 1514-1339 ($NO_2$). $^1H$ NMR (850 MHz, $CDCl_3$): δH 8.29, 8.28 (2H, 2 d, Ar—H), 7.65, 7.64 (2H, 2 d, Ar—H), 5.65 (1H, br. s, —OH), 4.85 (1H, dd, 2-H), 4.60 (1H, dd, 2-H), 4.48 (1H, dd, 1-H). $^{13}C$ NMR (850 MHz, $CDCl_3$): δC 148.18, 144.95, 128.72, 127.01, 124.27, 69.98. 2-Nitro-1-(3-nitrophenyl)ethan-1-ol (3b). Mp 59° C. FTIR: vmax/cm-1 3517 (OH), 3080 (C—H), 1527 ($NO_2$). $^1H$ NMR (850 MHz, $CDCl_3$): δH 8.70 (1H, s, Ar—H), 8.48 (1H, d, Ar—H), 8.23 (1H, d, Ar—H), 7.89 (1H, t, Ar—H), 5.62 (1H, br. s, OH), 5.08 (1H, dd, 2-H), 4.91 (1H, dd, 2-H), 4.62 (1H, dd, 1-H). $^{13}C$ NMR (850 MHz, $CDCl_3$): δC 148.74, 140.65, 132.11, 130.46, 128.64, 124.42, 123.67, 69.85.

2-Nitro-1-(2-nitrophenyl)ethan-1-ol (3c). Mp 60° C. FTIR: vmax/cm-1 3478 (OH), 3107 (C—H), 1511 ($NO_2$). $^1H$ NMR (850 MHz, $CDCl_3$): δH 7.96 (1H, d, Ar—H), 7.75 (1H, t, ArH), 7.56 (2H, dsd, Ar—H), 6.03 (1H, br. s, OH), 4.86 (1H, dd, 2-H), 4.56 (1H, dd, 2-H), 4.47 (1H, dd, 1-H). $^{13}C$ NMR (850 MHz, $CDCl_3$): δC 135.56, 134.76, 130.12, 128.96, 126.18, 125.01, 66.90.

1-(3,5-Dibromophenyl)-2-nitroethan-1-ol (3d). Mp>300° C. FTIR: vmax/cm-1 3202 (OH), 3073 (C—H), 1548-1378 ($NO_2$), 684 (C—Br). $^1H$ NMR (850 MHz, $CDCl_3$): δH 7.46 (1H, d, Ar—H), 7.41 (2H, d, Ar—H), 7.28 (1H, s, Ar—H), 5.41 (1H, br s, —OH), 4.78 (1H, dd, 2-H), 4.62 (1H, dd, 2-H), 4.5 (1H, dd, 1-H), 3.94, 3.97 (δH, 2 s, 2 —$OCH_3$). $^{13}C$ NMR (850 MHz, $CDCl_3$): δC 141.80, 134.57, 130.99, 127.90, 123.60, 69.56. 4-Bromo-2-(1-hydroxy-2-nitroethyl)-6-nitrophenol (3e). Mp>300° C. FTIR: vmax/cm-1 3500-3700 (2 OH), 1523-1341 (2 $NO_2$), 520 (C—Br). $^1H$ NMR (850 MHz, $CDCl_3$): δH 10.40 (1H, br s, —OH), 8.49 (1H, d, Ar—H), 8.28 (1H, d, ArH), 7.28 (1H, br. s, —OH), 4.83 (1H, dd, 2-H), 4.52 (1H, dd, 2-H), 4.35 (1H, dd, 1-H). $^{13}C$ NMR (850 MHz, $CDCl_3$): δC 150.18, 139.45, 138.06, 128.01, 127.40, 126.82, 111.87, 65.40. 1-[4-(Dimethylamino)phenyl]-2-nitroethan-1-ol (3f). Mp 70-72° C. FTIR: vmax/cm-1 3317 (OH), 3048 (C—H), 1589-1368 ($NO_2$), 1125 (C—N). $^1H$ NMR (850 MHz, $CDCl_3$): δH 7.76 (2H, d, Ar—H), 6.73 (2H, d, Ar—H), 5.39 (1H, br s, OH), 4.75 (1H, dd, 2-H), 4.65 (1H, dd, 2-H), 4.50 (1H, dd, 1-H), 3.11 (δH, 1 s, 2 —$OCH_3$). $^{13}C$ NMR (850 MHz, $CDCl_3$): δC 154.38, 131.50, 128.07, 125.14, 111.02, 71.11, 40.10, 40.08. 1-(4-Bromophenyl)-2-nitroethan-1-ol (3g). Mp 41° C. FTIR: vmax/cm-1 3530 (OH), 3034 (C—H), 1548-1340 ($NO_2$) 660 (C—H). $^1H$ NMR (850 MHz, $CDCl_3$): δH 7.57, 7.56 (2H, 2 d, Ar—H), 7.31, 7.30 (2H, 2 d, Ar—H), 5.44 (1H, br s, —OH), 4.78 (1H, dd, 2-H), 4.59 (1H, dd, 2-H), 4.51 (1H, dd, 1-H). $^{13}C$ NMR (850 MHz, $CDCl_3$): δC 137.07, 132.48, 131.03, 129.08, 127.65, 123.09, 70.36.

1-(4-Methoxyphenyl)-2-nitroethan-1-ol (3h). Mp>300° C. FTIR: vmax/cm-1 3456 (OH), 3004 (C—H) 1550-1378 ($NO_2$), 1160 (C-0). $^1H$ NMR (850 MHz, $CDCl_3$): δH 7.85, 7.84 (2H, 2 d, Ar—H), 7.02, 7.01 (2H, 2 d, Ar—H), 5.41 (1H, br s, —OH), 4.77 (1H, dd, 2-H), 4.66 (1H, dd, 2-H), 4.50 (1H, dd, 1-H), 3.90 (3H, 1 s, —OCH$_3$). $^{13}$C NMR (850 MHz, CDCl$_3$): δC 156.01, 132.05, 129.80, 127.31, 114.95, 67.78, 55.65. 1-(3,5-Dimethoxyphenyl)-2-nitroethan-1-ol (3i). Mp 86° C. FTIR: vmax/cm-1 3504 (OH), 3081 (C—H), 1509-1398 (NO$_2$), 1190 (C-0). $^1$H NMR (850 MHz, CDCl$_3$): δH 7.68 (1H, br s, Ar—H), 7.53 (2H, s, Ar—H), 5.41 (1H, br s, OH), 4.77 (1H, dd, 2-H), 4.58 (1H, dd, 2-H), 4.54 (1H, dd, 1-H), 3.94, 3.97 (δH, 2 s, 2 —OCH$_3$). $^{13}$C NMR (850 MHz, CDCl$_3$): δC 154.50, 149.62, 130.11, 126.92, 111.27, 110.39, 108.93, 70.88, 56.19, 56.01. 4-(1-Hydroxy-2-nitroethyl)-2-methoxyphenol (3j). Mp 75° C. FTIR: vmax/cm-1 3470-3181 (2 OH), 3020 (C—H), 1587-1373 (NO$_2$), 1150 (C—O). $^1$H NMR (850 MHz, CDCl$_3$): δH 9.85 (1H, br s, —OH), 7.448, 7.446 (3H, d, ArH), 5.42 (1H, br s, OH), 4.77 (1H, dd, 2-H), 4.63 (1H, dd, 2-H), 4.52 (1H, dd, 1-H), 3.99 (3H, s, —OCH$_3$). $^{13}$C NMR (850 MHz, CDCl$_3$): δC 147.15, 146.97, 135.01, 127.58, 114.38, 108.76, 70.96, 56.41.

REFERENCES (1) Liu, S.; Gao, W.-C.; Miao, Y.-H.; Wang, M.-C. J. Org. Chem. 2019, 84, 2652-2659.
(2) Markad, D.; Mandal, S. K. Dalton Trans. 2018, 47, 5928-5932.
(3) Kallitsakis, M. G.; Tancini, P. D.; Dixit, M.; Mpourmpakis, G.; Lykakis, I. N. J. Org. Chem. 2018, 83, 1176-1184.
(4) Sheldon, R. A. J. R. Soc., Interface 2016, 13, No. 20160087.
(5) Choudary, B. M.; Kantam, M. L.; Kavita, B. J. Mol. Catal. A: Chem. 2001, 169, 193-197.
(6) Seebach, D.; Beck, A. K.; Mukhopadhyay, T.; Thomas, E. Helv. Chim Acta 1982, 65, 1101-1133.
(7) Rosini, G.; Ballini, R.; Sorrenti, P. Synthesis 1983, 1983, 1014-1016.
(8) de Lange, B.; Hyett, D. J.; Maas, P. J.; Mink, D.; van Assema, F. B.; Sereinig, N.; de Vries, A. H.; de Vries, J. G. ChemCatChem 2011, 3, 289-292.
(9) Abdellattif, M. H.; Mokhtar, M. Catalysts 2018, 8, No. 133.
(10) Sun, L.-B.; Liu, X.-Q.; Zhou, H.-C. Chem. Soc. Rev. 2015, 44, 5092-5147.
(11) Shahid, A.; Ahmed, N. S.; Saleh, T. S.; Al-Thabaiti, S. A.; Basahel, S. N.; Schwieger, W.; Mokhtar, M. Solvent-Free Biginelli Catalysts 2017, 7, No. 84.
(12) Mokhtar, M.; Basahel, S. N.; Al-Angary, Y. J. Alloys Compd. 2010, 493, 376-384.
(13) Mokhtar, M.; Inayat, A.; Ofili, J.; Schwieger, W. Appl. Clay Sci. 2010, 50, 176-181.
(14) Mokhtar, M. Adsorpt. Sci. Technol. 2003, 21, 425-438.
(15) Gliński, M. Appl. Catal., A 2008, 349, 133-139.
(16) Cella, R.; Stefani, H. A. Tetrahedron 2009, 65, 2619-2641.
(17) Long, Z.; Liu, M.; Jiang, R.; Zeng, G.; Wan, Q.; Huang, H.; Deng, F.; Wan, Y.; Zhang, X.; Wei, Y. Ultrason. Sonochem. 2017, 35, 319-325.
(18) Banerjee, B. Ultrason. Sonochem. 2017, 35, 1-14.
(19) Cui, G.; Wang, F.; He, S.; Wei, M. RSC Adv. 2016, 6, 105406-105411.
(20) Olsbye, U.; Akporiaye, D.; Rytter, E.; Rønnekleiv, M.; Tangstad, E. Appl. Catal., A 2002, 224, 39-49.
(21) El-Shobaky, G. A.; Fagal, G. A.; Mokhtar, F. M. Appl. Catal., A 1997, 155, 167-178.
(22) Cavani, F.; Trifiro, F.; Vaccari, A. Catal. Today 1991, 11, 173-301.
(23) Yamaoka, T.; Abe, M.; Tsuji, M. Mater. Res. Bull. 1989, 24, 1183-1199.
(24) Naseem, S.; Gevers, B.; Boldt, R.; Labuschagne, F. J. W.; Leuteritz, A. RSC Adv. 2019, 9, 3030-3040.
(25) Radwan, N. R.; Turky, A. E.-M. M.; El-Shobaky, G. Colloids Surf., A 2002, 203, 205-215.
(26) Comelli, N. A.; Ruiz, M. L.; Aparicio, M. S. L.; Merino, N. A.; Cecilia, J. A.; Rodríguez-Castellón, E.; Lick, I. D.; Ponzi, M. I. Appl. Clay Sci. 2018, 157, 148-157.
(27) Kumar, P. S.; Selvakumar, M.; Babu, S. G.; Karuthapandian, S. Mater. Res. Bull. 2016, 83, 522-533.
(28) Sing, K. S.; Williams, R. T. Adsorpt. Sci. Technol. 2004, 22, 773-782.
(29) Sing, K. S.; Everett, D. H.; Haul, R.; Moscou, L.; Pierotti, R. A.; Rouquerol, J.; Siemieniewska, T. Pure Appl. Chem. 1985, 57, 603-619.
(30) Wagner, C.; Allison, J.; Rumble, J., Jr; Naumkin, A.; Kraut-Vass, A.; Powell, C. X-ray Photoelectron Spectroscopy Database (Version 3.0-3.4); National Institute of Standards and Technology (NIST): Gaithersburg, Md., 2000.
(31) Ghijsen, J.; Tjeng, L.-H.; van Elp, J.; Eskes, H.; Westerink, J.; Sawatzky, G. A.; Czyzyk, M. T. Phys. Rev. B 1988, 38, No. 11322.
(32) Wang, W.; Liu, Z.; Liu, Y.; Xu, C.; Zheng, C.; Wang, G. Appl. Phys. A: Mater. Sci. Process 2003, 76, 417-420.
(33) Diaz-Droguett, D.; Espinoza, R.; Fuenzalida, V. Appl. Surf. Sci. 2011, 257, 4597-4602.
(34) Elmhamdi, A.; Castañeda, R.; Kubacka, A.; Pascual, L.; Nandi, K.; Martinez-Arias, A. Appl. Catal., B 2016, 188, 292-304.
(35) Khairallah, F.; Glisenti, A. Surf. Sci. Spectra 2006, 13, 58-71.
(36) Aristizábal, A.; Contreras, S.; Barrabés, N.; Llorca, J.; Tichit, D.; Medina, F. Appl. Catal., B 2011, 110, 58-70.
(37) Singh, S.; Raj, T.; Singh, H.; Kanwar, J. S. J. Nanoelectron. Optoelectron. 2019, 14, 1468-1481.
(38) Wang, X.; Andrews, L. Inorg. Chem. 2005, 44, 9076-9083.
(39) Hsu, J.-P.; Nacu, A. Colloids Surf., A 2005, 262, 220-231.
(40) Zu, G.; Shen, J.; Wei, X.; Ni, X.; Zhang, Z.; Wang, J.; Liu, G. J. Non-Cryst. Solids 2011, 357, 2903-2906.
(41) Crivello, M.; Pérez, C.; Herrero, E.; Ghione, G.; Casuscelli, S.; Rodriguez-Castellon, E. Catal. Today 2005, 107-108, 215-222.
(42) Li, F.; Jiang, X.; Zhao, J.; Zhang, S. Nano Energy 2015, 16, 488-515.
(43) Ren, H.; Xu, C.-H.; Zhao, H.-Y.; Wang, Y.-X.; Liu, J.; Liu, J.-Y. J. Ind. Eng. Chem. 2015, 28, 261-267.
(44) Hopland, E. R. Master Thesis, NTNU, 2015.
(45) Zhou, Y.; Wu, J.; Lemmon, E. W. J. Phys. Chem. Ref. Data 2011, 40, No. 043106.
(46) Trost, B. M. Angew. Chem., Int. Ed. 1995, 34, 259-281.
(47) Montero, J. M.; Brown, D. R.; Gai, P. L.; Lee, A. F.; Wilson, K. Chem. Eng. J. 2010, 161, 332-339.
(48) Montero, J. M.; Gai, P.; Wilson, K.; Lee, A. F. Green Chem. 2009, 11, 265-268.
(49) Kurti, L.; Czakó, B. Strategic Applications of Named Reactions in Organic Synthesis; Elsevier, 2005.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of catalyzing a chemical reaction comprising contacting reactants of the chemical reaction with a catalytically effective amount of a CuMgAl ternary oxide catalyst, wherein the reactants include a nitroalkane and an aldehyde or a ketone.

2. The method of claim 1, wherein the reaction is conducted in the presence of ultrasonic irradiation.

3. The method of claim 1, wherein the nitroalkane is nitromethane, the aldehyde is an aryl aldehyde and reaction products include one or more β-nitro-alcohols.

4. The method of claim 1, further comprising, after the reaction is complete,
recovering and reusing the CuMgAl ternary oxide catalyst, wherein the steps of recovering and reusing are performed at least 5 times without diminished catalytic activity of the CuMgAl ternary oxide catalyst.

5. The method of claim 4, further comprising, after the step of recovering, reusing the CuMgAl ternary oxide catalyst to catalyze another chemical reaction.

6. A method of making one or more β-nitro-alcohols, comprising
combining 4-nitrobenzaldehyde, nitromethane and a CuMgAl ternary oxide catalyst in a reaction vessel;
exposing the reaction vessel to ultrasonic energy for a period of time sufficient to convert the 4-nitrobenzaldehyde and the nitromethane to the one or more β-nitro-alcohols; and
recovering the one or more β-nitro-alcohols.

7. The method of claim 6, wherein the CuMgAl ternary oxide catalyst is CuMgAl-I or CuMgAl-II.

8. The method of claim 6, wherein the CuMgAl ternary oxide catalyst is CuMgAl-I.

9. The method of claim 6, wherein the β-nitro-alcohols include 2-Nitro-1-(4-nitrophenyl)ethan-1-ol, 2-Nitro-1-(3-nitrophenyl)ethan-1-ol, 2-Nitro-1-(2-nitrophenyl)ethan-1-ol, 1-(3,5-Dibromophenyl)-2-nitroethan-1-ol, 4-Bromo-2-(1-hydroxy-2-nitroethyl)-6-nitrophenol, 1-[4-(Dimethylamino)phenyl]-2-nitroethan-1-ol, 1-(4-Bromophenyl)-2-25 nitroethan-1-ol, 1-(4-Methoxyphenyl)-2-nitroethan-1-ol, 1-(3,5-Dimethoxyphenyl)-2-nitroethan-1-ol and 4-(1-Hydroxy-2-nitroethyl)-2-methoxyphenol.

* * * * *